United States Patent [19]
Lyttle et al.

[11] Patent Number: 5,817,758
[45] Date of Patent: Oct. 6, 1998

[54] P-NITROBENZYL SIDE-CHAIN PROTECTION FOR SOLID-PHASE SYNTHESIS

[75] Inventors: Matthew H. Lyttle, Point Reye Sta.; Michael D. Hocker, Pacifica, both of Calif.

[73] Assignee: Terrapin Technologies, Inc., South San Francisco, Calif.

[21] Appl. No.: 485,582

[22] Filed: Jun. 7, 1995

[51] Int. Cl.$^6$ .............................. C07K 1/04; C07K 1/06; A61K 38/00

[52] U.S. Cl. .............................................. 530/334

[58] Field of Search .............................................. 530/334

[56] References Cited

U.S. PATENT DOCUMENTS

| | | | |
|---|---|---|---|
| 4,242,238 | 12/1980 | Colescott et al. | 260/8 |
| 4,855,407 | 8/1989 | Wang et al. | 530/334 |
| 5,288,514 | 2/1994 | Ellman | 435/4 |

FOREIGN PATENT DOCUMENTS

| | | |
|---|---|---|
| 1 493 658 | 4/1969 | Germany . |
| 2 253 924 | 5/1973 | Germany . |

OTHER PUBLICATIONS

Suzuki, K. et al. The phenacyl and nitrobenzyl esters to minimize side reactions during treatment of glutamyl peptides . . . Chem. Pharm. Bull. 25(10) 2613–2616, 1977.
M. D. Bachi et al., *J. Org. Chem.* (1972) vol. 37(22).
R. Balasuriya et al., *Tetrahedron Letters,* (1983) vol. 24(13), pp. 1385–1386.
M. Bodansky, *Peptide Chemistry,* Springer–Verlag, pp. 94–97 (1988).
Bunin et al., *J. Am. Chem. Soc.* (1992), vol. 114, pp. 10997–10998.
R.R. Chauvette et al., *J. Med. Chem.* (1975) vol. 18(4), pp. 403–408.
F. Cotton et al., *Advanced Inorganic Chemistry* (1980), 4th ed., John Wiley and Sons, Inc., p. 374.
K. T. Finley et al., *J. Org. Chem.* (1969), vol. 34(7), p. 2083.
D.T. Gish et al., *J. Am. Chem.* (1953) vol. 75, p. 950.
E. Guibe–Jampel et al., *Synthetic Communications,* (1982) vol. 12(3), pp. 219–223.
S. Hashiguchi et al.,*J. Chem. Soc. Perkin Trans.* (1988), vol. 1, pp. 2345–2352.
H. Kunz, *Angew. Chem. Int. Ed. Engl.* (1987), vol. 26, pp. 294–308.
H. Kunz, *Angew Chem. Int. Ed. Engl.* (1987), vol. 99, pp. 297–311.
S.R. Lammert et al., *J. Org. Chem.* (1978) vol. 43, p. 1243.
G. LeCorre et al., *Tetrahedron,* (1978) vol. 34, pp. 3105–3112.
M. H. Lyttle et al. in Smith, J.A. and Rivier, J.E. (eds.), *Peptides: Chemistry and Biology,* ESCOM Leiden, pp. 583–584.
P. J. Romanovskis et al., *7th American Peptide Symposium, Madison,* pp. 229–232 (1981).
J.E. Shields et al., *J. Am. Chem. Soc.* (1961) vol. 83, pp. 3066–3070.
K. Suzuki et al., *Chem. Pharm. Bull.* (1978) vol. 26(7), pp. 2269–2274.
Atherton, E. et al (1981) *J. Chem. Soc. Perkin Trans.* 1: 538–546.
Fields, G.B. (1990) *Int. Peptide Prot. Res.* 35: 161–214.
Lehninger *Biochemistry* pp. 117–119.
Merrifield, B. (1963) *J. Amer. Chem Soc.* 85:2149–2154.
Merrifield, B. (1986) *Science* 232:341–347.
Sheppard, R.C. et al (1982) *Int. J. Peptide Prot. Res.* 20: 451–454.
Wade, J.D. et al (1986) *Bioploymers* 25: S21–S37.
Deimer, K.–H., "Blockierung und Schutz der α–Carboxy–Funktion, 33.116.1, 4–Nitro–benzylester," in Houben–Weyl, Synthese von Peptiden, Teil I, Band XV/1, 1974, Thieme, G., Stuttgart XP002012127.
Prestidge, R.L. et al., "Use of Substituted Benzyl Esters as Carboxyl–Protecting Groups in Sold–Phase Peptide Synthesis," *J Org Chem* (1976) 41(15):2579–2583.
Raschig, A. et al., "Comparison of ρ–Nitrophenyl Residues as Carboxyl Protecting Groups in the Synthesis of Oligopeptides," in Peptides: Chemistry, Structure, Biology, pp. 347–349, 1975, Ann Arbor Science, Roderich, W. (ed), Meienhofer, J. (ed.), Ann Arbor, MI, U.S. XP002011945.
Suzuki, K. et al., "The β–Phenacyl and β–Nitrobenzyl Esters to Suppress Side Reactions during Treatment of Aspartyl Peptides with Hydrogen Fluoride," *Chem Pharm Bull* (1976) 24(12):3025–3033.
Suzuki, K. et al., "The γ–Phenacyl and γ–ρ–Nitrobenzyl Esters to Minimize Side Reactions during Treatment of Glutamyl Peptides with Hydrogen Fluoride–Anisole Mixture," *Chem Pharm Bull* (1977) 25(10):2613–1616.

*Primary Examiner*—Cecilia J. Tsang
*Assistant Examiner*—Michael Borin
*Attorney, Agent, or Firm*—Morrison & Foerster LLP

[57] ABSTRACT

Solid phase supported synthesis of peptides and other molecules using protecting groups comprising p-nitrobenzyl is described.

6 Claims, 5 Drawing Sheets

SAME TETRAPEPTIDE, MADE WITH BOC LYS

FIG. 4E

SAME TETRAPEPTIDE, MADE WITH BOC LYS

FIG. 4F

SAME TETRAPEPTIDE, MADE WITH BOC LYS

P-NITROBENZYL SIDE-CHAIN PROTECTION FOR SOLID-PHASE SYNTHESIS

FIELD OF THE INVENTION

This invention relates to the solid-phase synthesis of peptides, and particularly relates to the use of p-nitrobenzyl esters, thioethers, ethers and carbamates for the protection of side-chains.

BACKGROUND OF THE INVENTION

Chemical peptide synthesis is a rapidly evolving area in the art, and methods of solid-phase peptide synthesis are well-described in the following references, hereby incorporated by reference: (Lehninger, *Biochemistry*, pp. 117–119; Merrifield, B., *J. Amer. Chem. Soc.* 85:2149–2154 (1963); Merrifield, B., *Science* 232:341–347 (1986); Wade, J. D. et al., *Biopolymers* 25:S21–S37 (1986); Fields, G. B., *Int. J. Peptide Prot. Res.* 35:161 (1990); MilliGen Report Nos. 2 and 2*a*, Millipore Corporation, Bedford, Mass., 1987).

To execute solid phase synthesis, one end of the desired compound is attached to a solid support and additional components, which are bi or trifunctional building blocks, are added in synthetic cycles. First, one of the masked functional groups on the support is chemically deprotected, followed by coupling the next component, then selectively deprotecting the next point of attachment on the newly anchored group. The cycles are continued until the last component has been added. At the conclusion of the solid phase supported synthesis, additional chemical steps are performed to remove side chain protecting groups and cleave the molecule from the solid support.

Current methods utilize solid-phase synthesis, in which the C-terminal amino acid is covalently linked to an insoluble resin particle large enough to be separated from the fluid phase by filtration. Thus, reactants are removed by washing the resin particles with appropriate solvents using an automated programmed machine. The completed peptide chain is cleaved from the resin by a reaction which does not affect peptide bonds.

In the more classical approach, known as the "tBoc method," the amino group of the amino acid being added to the resin-bound C-terminal amino acid is blocked with tert-butyloxycarbonyl chloride (Tboc). This protected amino acid is reacted with the bound amino acid in the presence of the condensing agent dicyclohexylcarbodiimide, allowing its carboxyl group to form a peptide bond with the free amino group of the bound amino acid. The amino-blocking group is then removed by acidification with trifluoroacetic acid (TFA); and subsequently decomposes into gaseous carbon dioxide and isobutylene. These steps are repeated cyclically for each additional amino acid residue. A more vigorous treatment with hydrogen fluoride (HF) is common at the end of the synthesis to cleave the benzyl-derived side chain protecting groups and the peptide-resin bond.

More recently, the "Fmoc" technique has been introduced as an alternative synthetic approach, offering milder reaction conditions, simpler activation procedures and compatibility with continuous flow techniques. Here, the α-amino group is protected by the base labile 9-fluorenylmethoxycarbonyl (Fmoc) group. Fmoc differs from Thoc in that the benzyl side chain protecting groups are replaced by the more acid labile t-butyl derivatives. Deprotection with mild base solutions, e.g., 20% piperidine in dimethylformamide (DMF), are substituted for repetitive acid treatments and the final HF treatment is eliminated. A TFA solution is used instead to cleave side chain protecting groups and the peptide resin linkage.

At least three different peptide-resin cleavage agents can be used in the Fmoc technique using a substituted benzyl alcohol linker which can be cleaved with 95% TFA to produce a peptide acid, methanolic ammonia to produce a peptide amide, or 1% TFA to produce a protected peptide which can then be used in fragment condensation procedures, as described by Atherton, E. et al., *J. Chem. Soc. Perkin Trans.* 1:538–546 (1981) and Sheppard, R. C. et al., *Int. J. Peptide Prot. Res.* 20:451–454 (1982). Furthermore, highly reactive Fmoc amino acids are available as pentafluorophenyl esters or dihydrooxobenzotriazine ester derivatives, saving the step of activation used in the tBoc method.

Additionally, in the solid-phase synthesis of peptides, it is necessary to protect the various functional groups of the growing peptide chain and residues to be added to the chain when such substituents and side chains might interfere with peptide synthesis. An ideal candidate for a side chain protecting group in solid-phase supported peptide synthesis would have the ability to protect acids, and hydroxyl, sulfhydryl and amine groups. The protecting groups should also be stable to other conditions used during peptide synthesis, including conditions used to cleave N-terminal protecting groups, to deprotect orthogonal side chain protecting groups, and to remove a peptide from the solid phase to which it is attached.

SUMMARY OF THE INVENTION

One aspect of the present invention relates to a method for the solid-phase synthesis of a peptide, in which one or more acid, hydroxyl, sulfhydryl and amine substituents are protected with a p-nitrobenzyl group and such protected residues are attached to a conventional solid-phase support or to the N-terminus of a peptide attached to the resin. A further aspect of the invention relates to a method for deprotecting a peptide synthesized in solid phase that is protected with one or more p-nitrobenzyl groups, by treating the peptide with an effective amount of $SnCl_2$ and removing the resultant imino quinone reaction products.

In yet a further aspect of the present invention, an internal cyclic peptide is formed by condensing two deprotected side chains. The cyclized and linear chain peptides also may be cleaved from the solid support.

The invention also relates to a method for the synthesis on a solid phase support of any molecule or library of molecules containing amine, acid, hydroxyl or sulfhydryl substituents. This method includes the steps of protecting one or more acid, hydroxyl, sulfhydryl and amine substituents of a moiety to be incorporated into such a molecule with a p-nitrobenzyl group and attaching said protected moiety to a conventional solid-phase support or to a portion of the molecule already attached either directly or indirectly to the solid phase support.

MODES FOR CARRYING OUT THE INVENTION

In current practice, solid-phase supported peptide synthesis is frequently performed using base labile 9-fluorenylmethoxycarbonyl (Fmoc) as the protecting group for the N-terminal amino group of the growing peptide chain. Acid labile groups are used to protect the reactive side chains of each amino acid.

We hypothesized that an Fmoc compatible protection strategy could be developed using a p-nitrobenzyl moiety to protect appropriate groups on amino acid side chains that can interfere with peptide synthesis unless masked. To test this idea, cleavage conditions were sought which would cleanly remove these groups without destroying the product. Success in this endeavor has created a new tool which offers added versatility in solid-phase synthesis applications such as combinatorial chemistry. Complex products, such as cyclic peptides and glycopeptides, for example, can be synthesized using the new method, with minimal deviation from well established protocols for peptide synthesis.

The use of nitrobenzyl protective groups for peptide synthesis in solution has been demonstrated, although application of this strategy to solid-phase synthesis has not been reported. For example, p-Nitrobenzyl esters, ethers, thioethers and carbamate derivatives have been used successfully for the protection of these functional groups in solution phase synthesis. See, for example, LeCorre, G. et al. *Tetrahedron* (1978) 34:3105; Guibe-Jampel, E. et al. *Synthetic Communications* (1982) 12(3):219–223; Bachi, M. D. et al. *J Org Chem* (1972) 37(22); Chauvette, R. R. et al. *J Med Chem* (1975) 18(4):403; Balasuriya, R. et al. *Tet Let* (1983) 24(13):1385–1386; Lammert, S. R. et al. *J Org Chem* (1978) 43:1243; Gish, D. T. et al. *J Am Chem* (1953) 75:950; Hashiguchi, S. et al. *J Chem Soc Perkin Trans* (1988) 1; Suzuki, K. et al. *Chem Pharm Bull* (1978) 26(7):2269–2274; Shields, J. E. et al. *J Am Chem Soc* (1961) 83:3066; and Romanovskis, P. J. et al. *7th American Peptide Symposium. Madison* (1981)), the disclosures of which are incorporated herein by reference.

In the foregoing references, for example, the Balasuriya et al. paper used 30% $H_2O_2$ in 6 N aqueous ethanolic sodium hydroxide at 50° C. for six hours to deblock p-nitrobenzyl-protected bases and phenols. Suzuki et al. deblocked p-nitrobenzyl-protected dipeptides through catalytic dehydrogenation over 10% palladiumcarbon or deprotected the peptide with zinc powder in 80% acetic acid at 0° C. in reactions to deprotect a β-carboxyl group. The paper by Bachi et al. similarly reported the removal of S-p-nitrobenzyl protecting groups using hydrogenation in the presence of 10% palladium-charcoal, thus following a similar approach to the protection of sulfhydryl protecting groups. These approaches, however, were not applied to solid-phase peptide synthesis, and have obvious shortcomings.

Necessary for success of a p-nitrobenzyl protection scheme in solid-phase peptide synthesis is an ability to withstand the various conditions of chemical exposure to which the protected monomer and incorporated protected residue are exposed during the various steps and cycles of peptide synthesis. From the actual synthesis to the final deprotection step, a useful p-nitrobenzyl derivative needs to be stable for shelf storage and for hours in room temperature solutions, and once incorporated into the peptide product, it must be sufficiently stable to withstand successive treatment cycles of activated amino acids, piperidine deprotections and washes with methylene chloride and DMF.

We have found that p-nitrobenzyl side chain protected Lys, Cys and Asp are stable under the conditions for peptide synthesis, and only become labile once subjected to the mild reducing conditions described below. Since reducing steps are not normally applied during the course of peptide synthesis, the p-nitrobenzyl protection scheme represents an orthogonal addition to the current side chain protection schemes; Boc (acid labile), Fmoc (base labile) and Benzyl (HF labile). It also appears to be stable to the conditions used to remove other orthogonal protecting groups, such as allyl (Lyttle, M. H. et al. in Smith, J. A. and Rivier, J. E. (eds.), *Peptides: Chemistry and Biology*, ESCOM Leiden, p. 583), from peptides containing the standard protecting groups.

Figure 1:
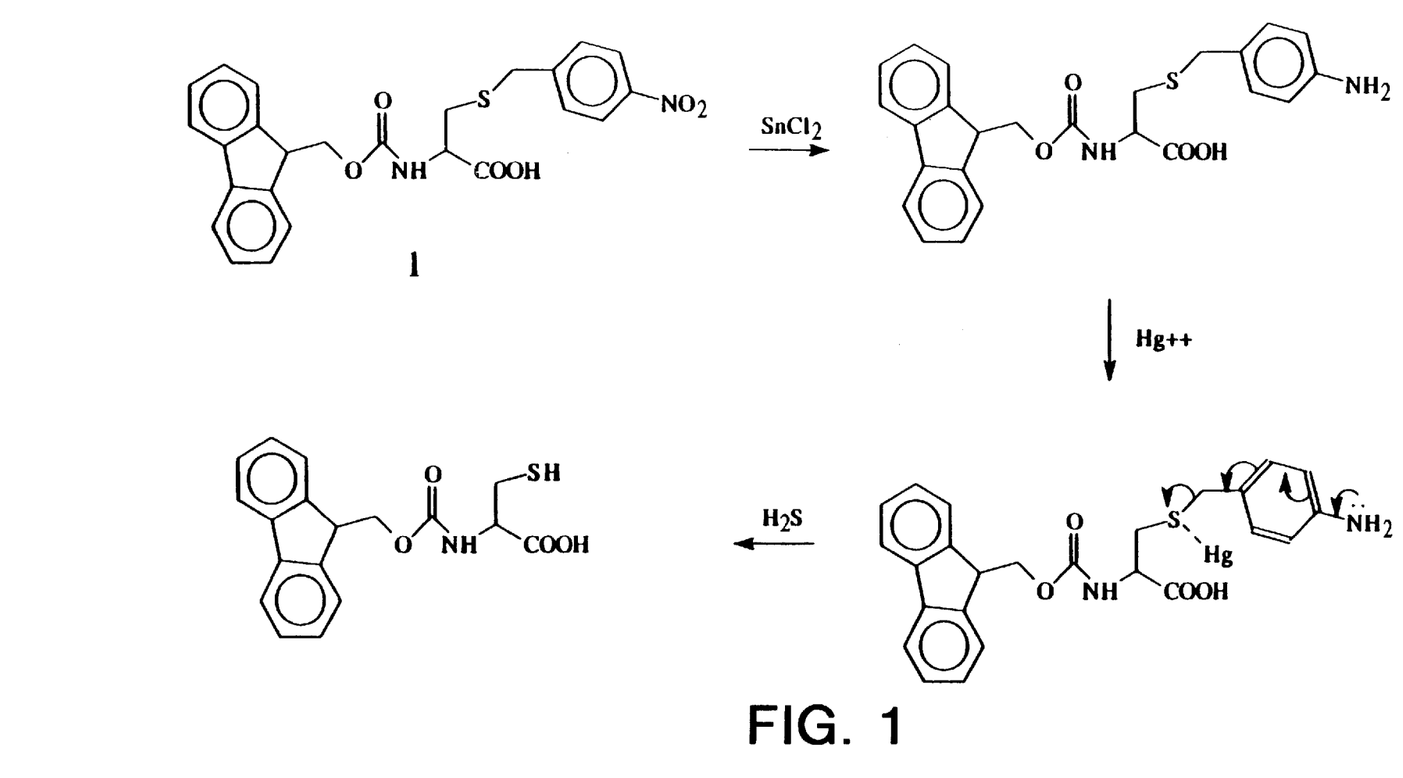
FIG. 1 illustrates the reductive cleavage of Cis-S-p-nitrobenzene.
Figure 2:
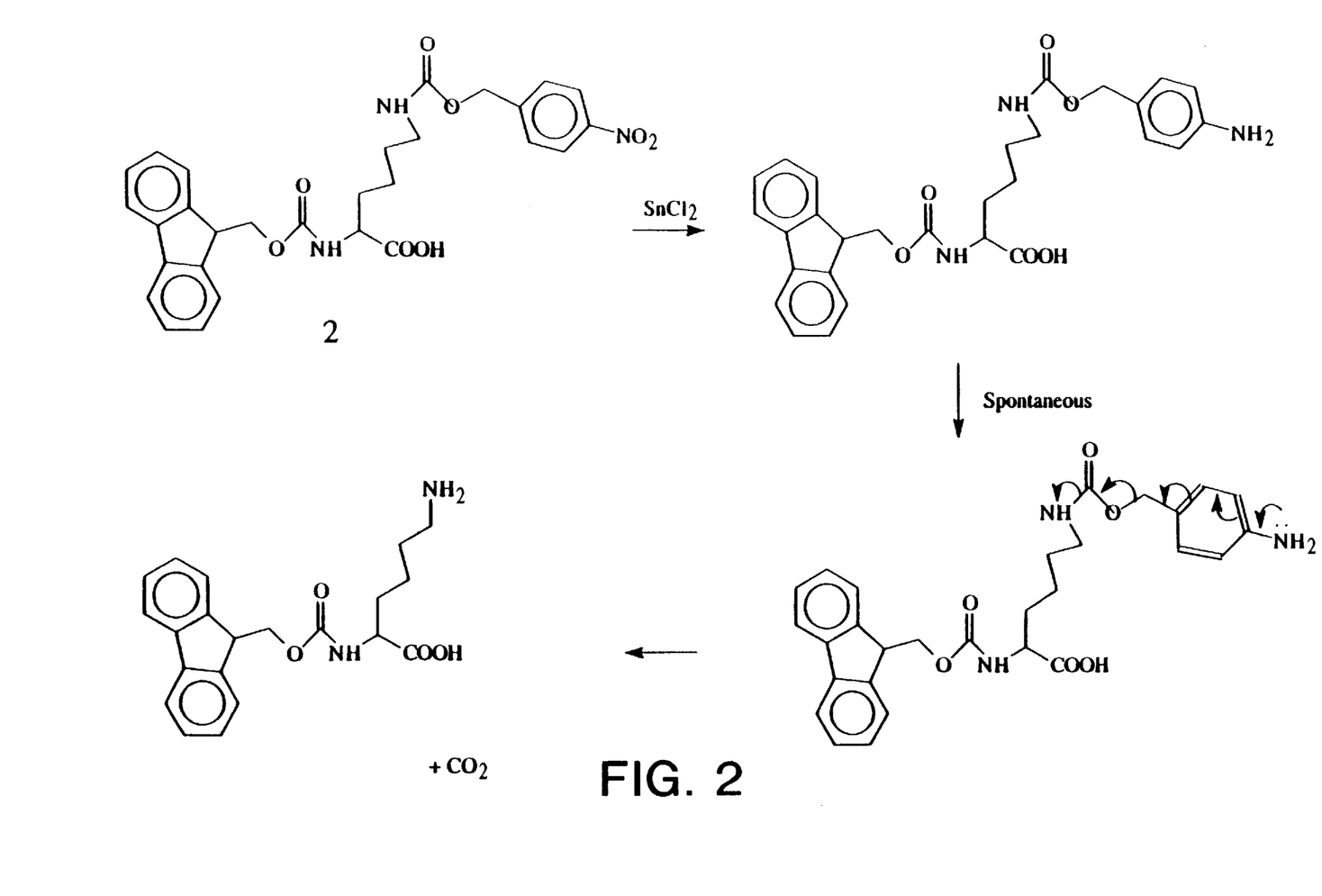
FIG. 2 illustrates the reductive cleavage of Lys-p-nitrobenzene.
Figure 3:
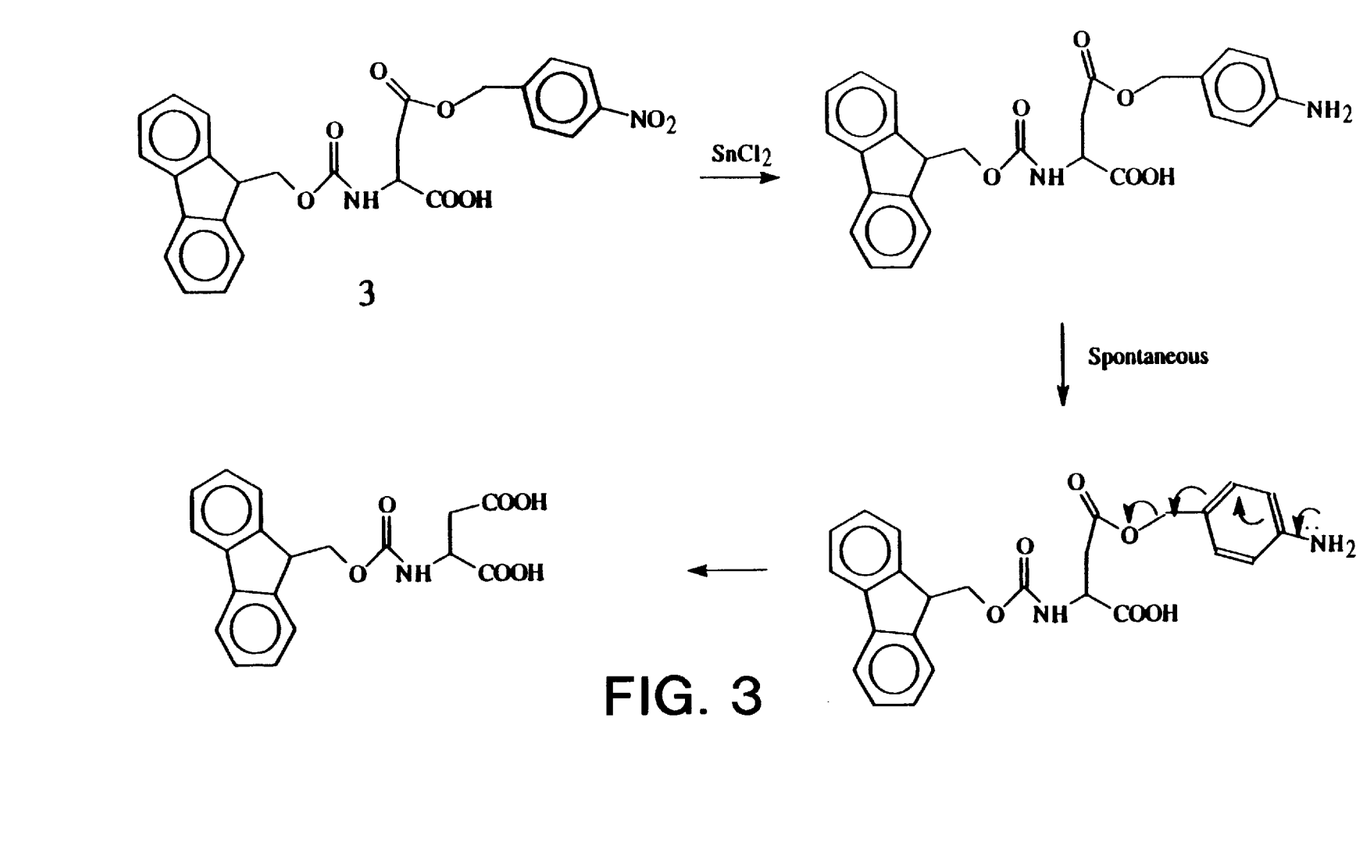
FIG. 3 illustrates the reductive cleavage of Asp-O-p-nitrobenzene.
Figure 4A:
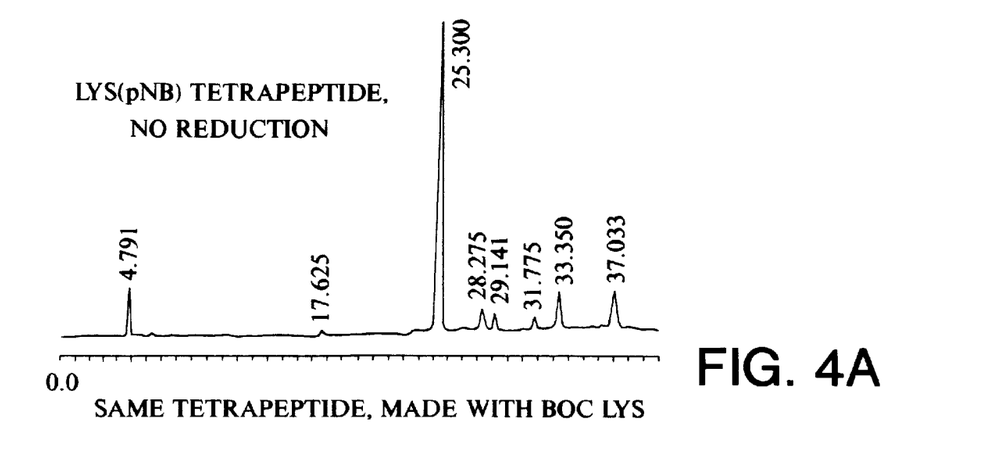
FIG. 4 shows the time course for Lys-p-nitrobenzene deprotection.
Figure 4B:
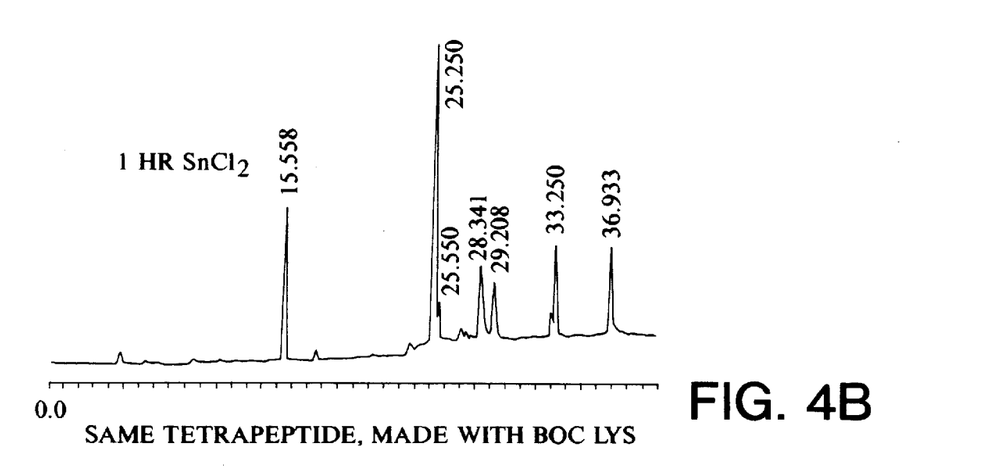
Figure 4C:
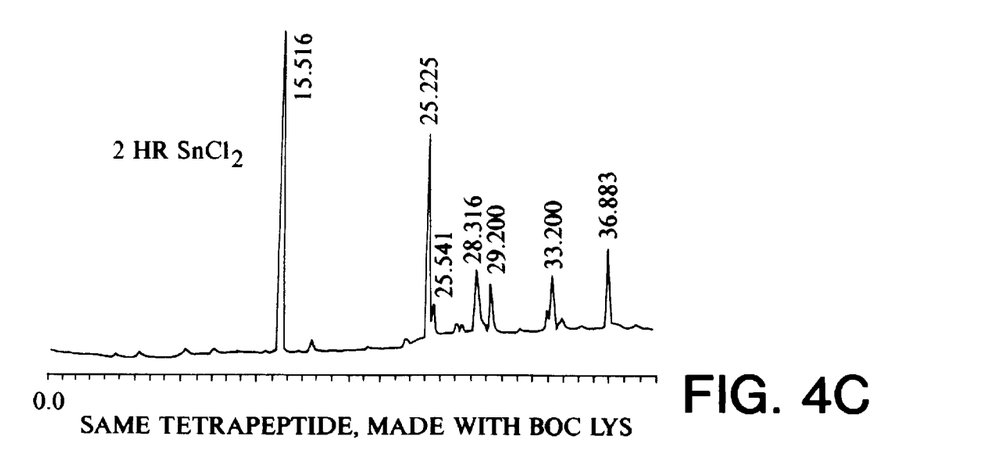
Figure 4D:
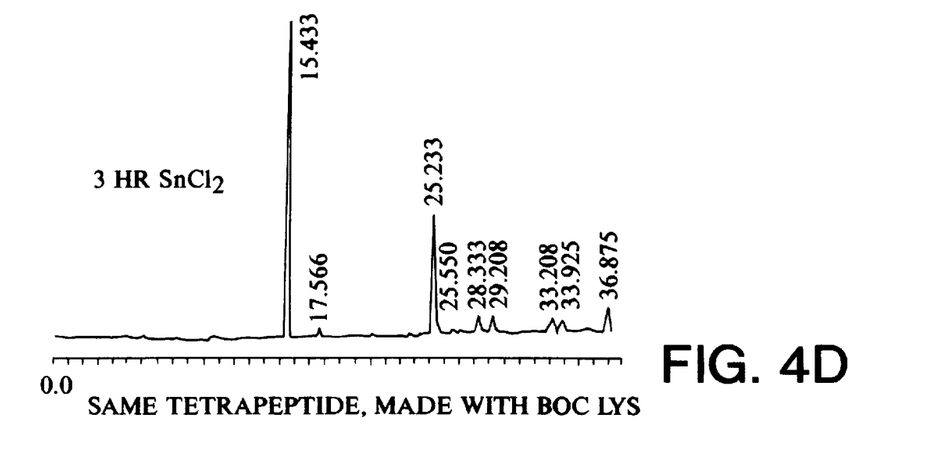
Figure 4E:
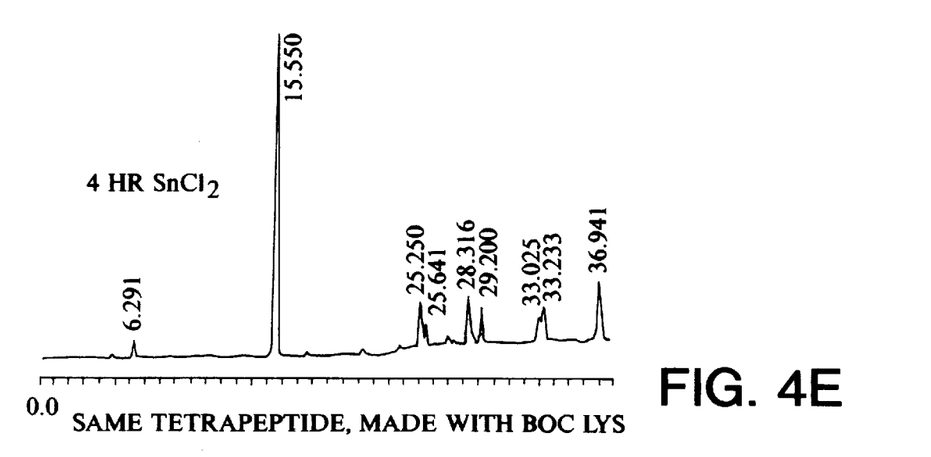
Figure 4F:
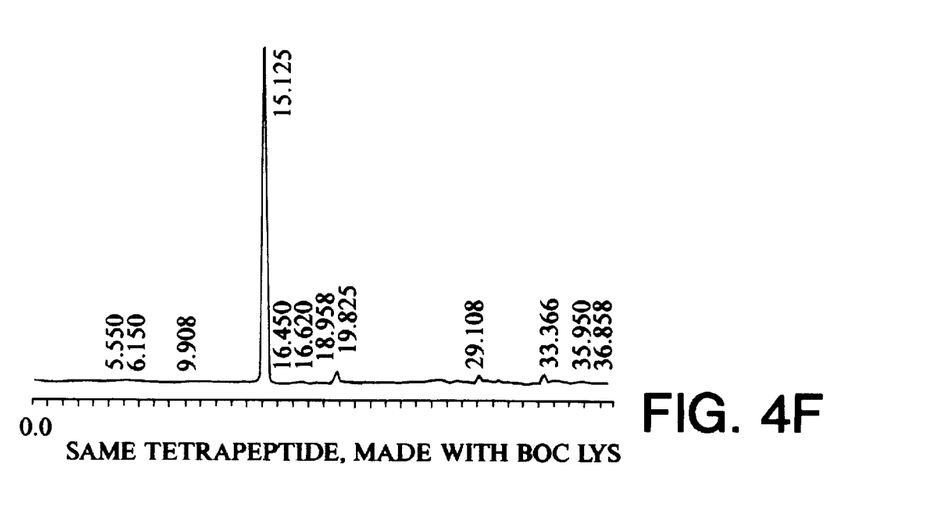

Deprotection of the p-nitrobenzyl derivatives occurs through a reductive elimination process (LeCorre, G. et al. *Tetrahedron* (1978) 34:3105; Guibe-Jampel, E. et al. *Synthetic Communications* (1982) 12(3):219–223). The reduction of the nitro group forms an electron donating p-aminobenzyl intermediate which then undergoes a 1,6-elimination to yield the corresponding unmasked functionality and a quinone. See FIGS. 1–3. p-Aminobenzyl thioethers, however, do not eliminate and require Hg salt-$H_2S$ treatments (Guibe-Jampel, E. et al. *Synthetic Communications* (1982) 12(3):219–223; Bachi, M. D. et al. *J Org Chem* (1972) 37(22)). Application of the reduction to solid-phase synthesis generally is best carried out on the resin followed by thorough rinsing, leaving cleavage of the peptide as the final step before purification.

Reductive deprotection on the resin requires a soluble reducing agent, with the solvent being compatible with polystyrene resin swelling and inert to the deprotected peptide and resin linker. Reductive elimination reactions proceed best in proton donating solutions, and the solubility of $SnCl_2$ (Cotton, F. et al. *Advanced Inorganic Chemistry,* 4th ed., John Wiley and Sons, Inc., p. 374 (1980)) in various organic solvents and its ability to specifically reduce nitro groups (Bodanszky, M. *Peptide Chemistry*, Springer-Verlag, p. 95 (1988)) make it an ideal candidate as the reducing agent. Various catalysts such as triphenyl phosphine and phenol are known to catalyze these reactions (Cotton, F. et al. *Advanced Inorganic Chemistry*, supra, p. 1237) and have also been explored. Our application of these conditions to solid-phase peptide synthesis has yielded a deprotection method for the resin bound peptide, with standard TFA cleavage then giving the deprotected crude peptide.

EXAMPLE 1

Preparation of $N^\alpha$-Fmoc-S-(paranitrobenzyl) cysteine

A solution of 500 ml of water and 20 ml of 28–30% $NH_4OH$ was sparged with argon for 10 min. 20 g (0.165 M) of L-Cysteine was dissolved into the solution. 35.7 g (0.165 M) of p-nitrobenzylbromide dissolved in 200ml of tetrahydrofuran (THF) was added dropwise to the stirring solution under argon. After 1 hour the THF was removed in vacuo. The solution was then chilled to 0° C. whereupon yellow-white needle crystals formed. These were collected by vacuum filtration and dried under a high vacuum overnight. 40.2 g of cys-SpNB, 95.5% yield, was recovered. 20 g of the cys(pNB) was suspended in 300ml of a 3:1 water: THF solution Enough 4 N $Na_2CO_3$ was added to bring the pH to 9, which dissolved the compound leaving a clear yellowish solution. 40 g (0.119 M) of Fmoc-OSu dissolved in 400ml of THF was added dropwise to the stirring solution while the pH was maintained at 9.

The reaction mixture was stirred for four hours. The solution was diluted with 1 l of water and extracted twice with 300 ml of a 50/50 solution of ether and petroleum ether. The aqueous was acidified to pH 2 with concentrated HCl, forming a thick white precipitate. This was extracted with 300 ml of EtOAc. The organic layer was dried over $Na_2SO_4$ filtered, and the filtrate was brought to cloud point by adding petroleum ether. The solution was chilled to 0° C. overnight. A fine layer of white crystals formed and were collected by filtration. This was dried under a high vacuum to give 20.91 g (55% yield) of a crystalline solid. mp 128°–130°. $^1$H NMR ($D_6$DMSO) δ:8.5(d,1H),8.1(d,2H),7.9(D,2H). 7.8(d,2H),7.7 (dd,2H),7.6(d,2H),7.3(d,2H), 5.3(d,2H),4.4(m,1H),4.2(m, 1H),2.8(s,2H),2.3(m,2H). M/e 502.87. (MNa+Calc'd 501.51).

EXAMPLE 2

Synthesis of $N^α$-Fmoc-Nε-(carbonyloxyparanitrobenzyl) lysine 30 g (0.198 M) of Lysine and 20.5 g (0.128 M) of $CuSO_4$ were suspended in 200 ml of water. A 4N solution of NaOH was added to produce a clear purple-blue solution with a pH of 9, and 50 ml of THF was added. 25 g (0.116 M) of p-nitrobenzyl chloroformate was dissolved in 100 ml of THF and was added dropwise to the stirring solution while the pH was maintained at 9. The reaction was stirred for four hours.

The solution was filtered, collecting a light blue solid. The solid was resuspended in water and filtered. The washed material was again resuspended in 800 ml of water and the pH was adjusted to 1 with HCl. 40 g (0.111 M) of EDTA was added and the solution was stirred magnetically over night. The solution was filtered and NaCl was added to near saturation point. The solution was cooled to 0° C. whereupon a white precipitate formed. After 1 hour the precipitate was collected by filtration. The solid was suspended in 300 ml of a solution of 30% THF/water. A 4 N solution of $Na_2CO_3$ was added to pH 9 causing the solution to go clear. 40 g (0.119 M) of Fmoc-OSu dissolved in 300 ml of THF was added dropwise to the dissolved lys(pNB) solution. The pH was maintained at 9.

After 4 hours the reaction mixture was diluted with 1 l of water. In a separatory funnel, the reaction mixture was washed twice with a 50/50 mixture of ether/pet ether. The aqueous layer was acidified to pH 2 with HCl, which formed a thick white-yellow paste. This was extracted with 300 ml of EtOAc. The EtOAc was dried over $MgSO_4$ and filtered. The solution was brought to cloud point with pet ether and then chilled to 0° C. Fine white-yellow crystals were induced to form upon scratching the flask and more crystals were obtained by adding additional pet ether. The crystals were isolated by filtration and dried under a high-vac to give 23.6 g (73% yield), mp 131°–133°. $^1$H NMR ($D_6$DMSO) δ:8.1(d,2H), 7.9(d,2H). 7.8(d2H),7.7(d,2H),7.6(dd,2H),7.5 (d,1H), 7.3(dd,2H),5.3(s,2H),4.8(d,2H),4.6(m,1H),4.0(m, 1H),2.9(m, 2H), 1.6 (m,2H),1.2(m,4H). (M/e 571.31 MNa'calc'd 570.55).

EXAMPLE 3

$N^α$-Fmoc-β-paranitrobenzoyl aspartic acid 10 g (.072 M) of L-aspartic acid was suspended in 100 ml of dioxane. 1.5 eq (16.5 g, .108 M) of p-nitrobenzyl alcohol and 10 ml of $H_2SO_4$ were added and the reaction mixture was refluxed for two hours. The reaction was allowed to cool to room temperature and was neutralized with pyridine, which caused a thick yellow paste to form. The solvent was decanted off and the solid was dissolved in 300 ml of water. In a separatory funnel, the aqueous layer was washed twice with 200 ml EtOAc. The aqueous was chilled to 40° C. overnight, and yellowish-brown needle crystals formed. These were collected by filtration and dried in vacuo to give 4.5 g of a crystalline solid. This was suspended in 200 ml of a 30% aqueous THF solution. A 4 N solution of $Na_2CO_3$ was added, raising the pH to 9 and causing the solution to clarify. 5.5 g (0.016 M) of Fmoc-OSu was dissolved in 100 ml of THF and was added dropwise to the Asp(pNB) solution while the pH was maintained at 9.

After four hours the reaction mixture was diluted with 500ml of water, and washed twice in a separatory funnel with 200 ml of a 50/50 mixture of ether and pet ether. The aqueous layer was acidified to pH 2 with concentrated HCl, causing a thick yellowish paste to form. This was extracted with 300 ml of EtOAc, dried over $MgSO_4$ filtered and brought to a cloud point with pet ether. The solution was chilled to 0° C. in an ice bath, and crystallization was induced by scratching the wall of the flask. The crystals were collected by filtration and dried under a high vac to give 6.3g, 80% yield. mp 107°–109°. $^1$H NMR ($D_6$DMSO) δ:8.2(d,2H) ,7.9(D,2H) . 7.85(d,1H), 7.8(d,2H),7.7(d,2H), 7.5(dd,2H),7.3(dd,2H),5.3(s,2H), 4.7(d,2H),4.5(m,1H),4.2 (m,1H),2.9(dd,1H),2.8(dd,1H). M/e 514.84 (MNa+ calc'd 513.46).

EXAMPLE 4

Solid-phase Synthesis

Solid-phase peptide synthesis was performed with standard protocols using a Biosearch SAM II automated peptide synthesizer. The tetrapeptides were synthesized at a 2 g resin scale with 6 equivalents of amino acids per resin amino group, with 2 hr coupling times. Synthesis resins and conventional Fmoc amino acids were obtained commercially from Novabiochem. Diisopropylcarbodiamide, hydroxybenzotriazole and piperidine were obtained from Aldrich.

Solvents were obtained from VWR. After the synthesis was complete, the N terminal Fmoc was removed and the resin was washed and dried. For reductive cleavage, each g of peptide containing synthesis resin was treated with 25 ml of 0.21 M $SnCl_2$ in DMF which also contained 0.002 M HCl or 0.0016 M HOAc, and 100 μL of phenol. The resin was stirred with this mixture for 4 hrs, and was rinsed several times with DMF followed by methanol. The resin was dried. The peptides were cleaved from the resin with a 2 hr treatment of 75% TFA/$CH_2Cl_2$, followed by removal of this solvent under a nitrogen stream. Peptides for HPLC analysis were dissolved completely in acetonitrile-water mixtures.

EXAMPLE 5

Benzene Sulfinic Acid Scavenger Treatment 50 mg of resin containing a p-nitrobenzyl side chain protected peptide was treated with 50 mg of $SnCl_2$ in 1 mL of DMF to which 25 ml of 1 N HCl in ether was added. The mixture was stirred for 5 hrs, and the resin was washed several times in a sintered glass funnel with DMF followed by methanol. The resin was again suspended in 1 mL of DMF, and 25 mg of benzene sulfinic acid was added, along with 25 ml of 1 N HCl in ether. The mixture was stirred for 30 min., and rinsed as before. The peptide was cleaved from the resin with 1 ml 75% TFA in $CH_2Cl_2$ containing 25 μl anisol and precipitated by adding ether to the TFA, after the resin was removed. The product contained a slight yellow tinge, in contrast to the dark orange products obtained without the sulfinic acid step.

EXAMPLE 6

Synthesis of Tetrapeptides $N^\alpha$-Fmoc-(S-paranitrobenzyl)cysteine (1) or "Fmoc Cys (pNB)", $N^\alpha$-Fmoc-(Nγcarbonyloxyparanitrobenzyl)lysine (2) or "Fmoc Lys(pNB)", and $N^\alpha$-Fmoc-aspartic acid-β-paranitrobenzoate) (3) or "Fmoc Asp (OPNB)" were synthesized and incorporated into the automated synthesis of individual tetrapeptides using standard Fmoc methodology. Each p-nitrobenzyl protected resin bound peptide was deprotected under various conditions and the product tetramer cleaved with TFA and analyzed by HPLC. The analogous peptide prepared through the standard acid labile side chain protection (Boc for lys and asp, trityl for cys) was used to establish the HPLC peak elution time of the intended product.

The resin bound peptide with the sequence phe-gly-cys (S-paranitrobenzyl)-leu was prepared, using solid-phase synthesis. Several reductive deprotection cocktails were tested on the resin, followed by cleavage of the peptide with TFA and analysis of the products by HPLC. The HPLC data indicated that $SnCl_2$/HCl worked best with 70% reduction of the protected peptide in 3 hours and little or no effect with other reducing agents, $NaSH/NH_4OH$ and $Na_2S/NH_4OH$. Also, HOAc was substituted for HCl in the $SnCl_2$ mixture, which showed the same rate of reduction. The $SnCl_2$ treatment was performed on the free p-nitrobenzyl protected tetramer and the reduction rate was monitored by TLC to compare with the resin bound reaction. The free peptide reduction rate was the same as that observed with the resin bound peptide. Eight different solvents were then tested with $SnCl_2$/HCl (See Table 1).

TABLE 1 pNB Reductive Deprotection Solvent Mixtures

| Solvent | Peak Ratios* |
|---|---|
| 75% Acetone in DMF | 20% |
| 50% MeOH in DMF | 42 |
| 100% DMF | 63 |
| 50% THF in DMF | 35 |
| 50% Toluene in DMF | 40.5 |
| 50% Toluene in MeCl | 18 |
| 50% MeCl in DMF | 53 |
| 50% MeOH in MeCl | 19 |

*Ratios are the area of the reduced tetrapeptide divided by the total area of unreduced and reduced peptide, in %

DMF was significantly the best solvent for the reduction with a 22% faster rate over the next best solvent. The $SnCl_2$-DMF reduction solution was then doped with $H_2SO_4$, triphenyl phosphine, and phenol as catalysts for the reduction. Test solutions were~0.02 M with these reagents. Although the reaction was not catalyzed, the phenol appeared to diminish the extraneous peaks that formed during the reduction. With Fmoc-Cys(S-trityl), the tetramer phe-gly-cys-leu was prepared and coinjected on HPLC with the above peptide. The two did not co-elute, indicating that although the p-nitro group had been reduced, an additional Hg treatment would be needed to remove the group, in accordance with the literature (Bachi, M. D. et al. *J Org Chem* (1972) 37(22)). The sample was successfully reduced using the optimized reduction conditions and, after rinsing, a 1 hour DMF/HgOAc treatment on the resin followed by a TFA/$H_2S$ cleavage. This provided the fully deprotected peptide, which co-eluted with the standard. A mass spectrum confirmed the identity of the peptide made with the new method.

Corresponding residues were synthesized and the tetramer phe-gly-lys(Nγcarbonyloxyparanitrobenzyl)-leu was prepared as above. With the optimum conditions determined, the time course of the cleavage reaction was monitored by HPLC, and FIG. 4 shows the disappearance of the protected peptide in 4 hours. An HPLC trace of the same peptide sequence made with Boc protected lysine and cleaved with TFA is included to show that the final products were the same using the two chemistries. The deprotection was also tried with the panel of catalysts. Again no catalytic activity was found although phenol was effective in eliminating extra peaks in the HPLC trace. Co-elution of the reference peptide prepared with Boc protection confirmed the identity of the peptide. Analogous results were obtained with the corresponding tetrapeptide made with Fmoc-Asp (paranitrobenzoate), phe-gly-asp(paranitrobenzoate)-leu.

Substitution of milder acid HOAc for HCl is a beneficial change, to reduce the chance of unwanted acid removal of other protecting groups, such as Boc, in an orthogonal synthesis. The fact that the free peptide underwent reduction at the same rate as the resin bound tetramer demonstrates that swelling of the resin in DMF is adequate for good permeation with the deprotection cocktail. TLC studies showed that Boc side chain protected lys, asp and glu were unaffected by the mildly acidic conditions of the $SnCl_2$ reductive cleavage.

The tetramer studies that we describe demonstrate that the p-nitrobenzyl protecting groups are stable under the conditions of peptide-resin cleavage, which conventionally requires exposure to TFA for 2 hrs. These observations, taken together, further demonstrate the orthogonality of our disclosed method with the standard Boc side chain protection scheme. The p-nitrobenzyl protecting group on cys also withstood treatment with HgOAc/$H_2S$, which will allow complex manipulations of peptides containing multiple cysteine residues. The standard cys-trityl protecting group was also unaffected by the reductive cleavage mixture, again shown by TLC.

There are reports that the highly colored quinone generated during deprotection becomes a problem upon Purification (LeCorre, G. et al. *Tetrahedron* (1978) 34:3105) with the final products contaminated with a yellow color. Ideally, the quinone should be washed off the resin after deprotection, but a scavenger would guarantee removal of the quinone. Sulfates and sulfites are known to react with imines (Finley, K. T. et al. *J Org Chem* (1969) 34(7):2083). We found that addition of benzene sulfinic acid in DMF containing 1 N HCl in anhydrous ether after the 4 hr treatment with $SnCl_2$ removed almost all of the yellow color from peptides deprotected with the $SnCl_2$ cocktail, and that spurious peaks in the crude sample were reduced, in the case of the lys tetrapeptide.

EXAMPLE 7

Synthesis of Cyclic Peptides

With the selective deprotection demonstrated for Lys and Asp, it now becomes possible to cyclize these residues while the otherwise fully protected peptide is on the resin, and the other reactive functional groups remain masked. These cyclization reactions have been demonstrated using the allyl based side chain protecting scheme for Ornithine, which contains an amine as the side chain, in analogy to Lys; and Glu, which has a carboxylic acid side chain, similar to Asp. This chemistry was applied to the synthesis of the cyclic peptide DQQNAFYEILH OPN—$NH_2$. The two side chains involved in the internal cyclic structure are shown in bold type. Details of the chemistry can be found in the literature (Lyttle, M. et al., in Smith, J. et al. (Eds.) *Peptides: Chemistry and Biology* (1992). Since the p-nitrobenzyl protecting scheme we have outlined works well on polystyrene, a significant improvement over the analogous allyl based chemistry in product yield would be expected because of the higher loading of polystyrene over the PEG copolymers needed for the allyl based chemistry.

EXAMPLE 8

Synthesis of non-Peptide Molecules

A great variety of different types of molecules, as well as small molecule libraries have been synthesized on solid support. One such system is that developed by Bunin et al., *J. Am. Chem. Soc.* 114: 10997–998 (1992) in which side chain protected amino acids are used in the solid phase synthesis of 1,4-benzodiazepin derivatives. These medicinally important derivatives of drugs such as diazepam (valium), were synthesized on a solid support using side chain protected amino acids asp and lys with acid labile side chain protecting groups. The p-nitro protecting group would be directly applicable for use in this system, and would also add scope to the reaction sequence by allowing cleavage under non-acidic conditions. A combinatorial library of such derivatives has also been reported, again by Ellman (U.S. Pat. No. 5,288,514), using similar chemistry. Both of these works underscore the potential utility of the p-nitrobenzyl method in the manufacturing of these compounds.

EXAMPLE 9

Synthesis of Proteins

In general, the use of milder conditions will improve the performance in the synthesis of longer peptides because the likelihood of acid catalyzed hydrolysis of the amide backbone, which would lead to destruction of the product during deprotection will be less. As well, many other acid sensitive compounds, such as glycol conjugated peptides, will be accessible, with the p-nitrobenzyl protection strategy, in analogy to those reported by Kunz et al., (Angew. Chem. v.99, (1987) p. 297; Angew. Chem. Intl. Ed. Engl. v. 26 (1987) p. 294) with the allyl methodology. We contemplate that this new solid phase protection scheme will be useful in the synthesis of compounds containing acid sensitive groups or backbones, and specifically will be applicable in the synthesis of compounds, as known in the art, using allyl protecting groups.

The foregoing examples and cited studies demonstrate a new protection-deprotection system for solid-phase synthesis, similar in scope to the allyl side chain protection strategy (Lyttle, M. et al., 1992), the disclosure of which is incorporated herein by reference, which is now becoming widely used in solid-phase synthesis, both of peptides and nonpeptides. The fact that cleavage occurs under mild conditions which do not remove the standard Boc side chain protecting groups will lend this method well to the formation of cyclic peptides with internal carboxylic and amine containing functionalities. Our new method provides a mild cleavage alternative to the hazardous and environmentally harmful hydrofluoric acid side chain deprotection scheme used with Boc N protected peptide synthesis methods.

We contemplate that the foregoing methods may be applied by one skilled in the art to the synthesis of longer peptides, and that such products may be purified by preparatory HPLC. Such products will be comparable to peptides of the same sequence made with the standard Fmoc method for color and purity. Similarly, a cyclic peptide may be made with the disclosed methods. Additionally, this method may be applied to the solid-phase synthesis of nonpeptides, such as DNA and RNA, glycoproteins and glycopeptides and other peptide conjugates. Thus, the scope of the invention we claim is not be limited by the foregoing specific embodiments. All of the references cited above are hereby incorporated by reference in their entirety.

We claim:

1. A method for the solid-phase synthesis of a peptide, comprising the steps of protecting one or more hydroxyl, sulfhydryl and/or amine substituents of an amino acid with a p-nitrobenzyl protecting group and attaching said protected amino acid to a conventional solid-phase support or to the N-terminus of a peptide attached to the support, treating the peptide on said solid support with an effective reducing amount of $SnCl_2$ and removing the resultant imino quinone reaction products.

2. A method for deprotecting a peptide synthesized on a solid phase support wherein said peptide is protected at least one hydroxyl, sulfhydryl or amine substituent with a p-nitrobenzyl protecting group which method comprises treating the peptide on said solid support with an effective reducing amount of $SnCl_2$ and removing the resultant imino quinone reaction products.

3. The method of claim 1 where said treating is with a solution of DMF, $SnCl_2$, phenol and anhydrous HCl.

4. The method of claim 3, further comprising the cleaving said synthesized peptide from the support with $TFA/CH_2Cl_2$.

5. The method of claim 2 in which an internal cyclic peptide is formed by condensing two deprotected side chains.

6. The method of claim 5 in which an internal functional group is attached to either the C or N terminus of the peptide, forming a cyclic structure.

* * * * *